Figure 1:
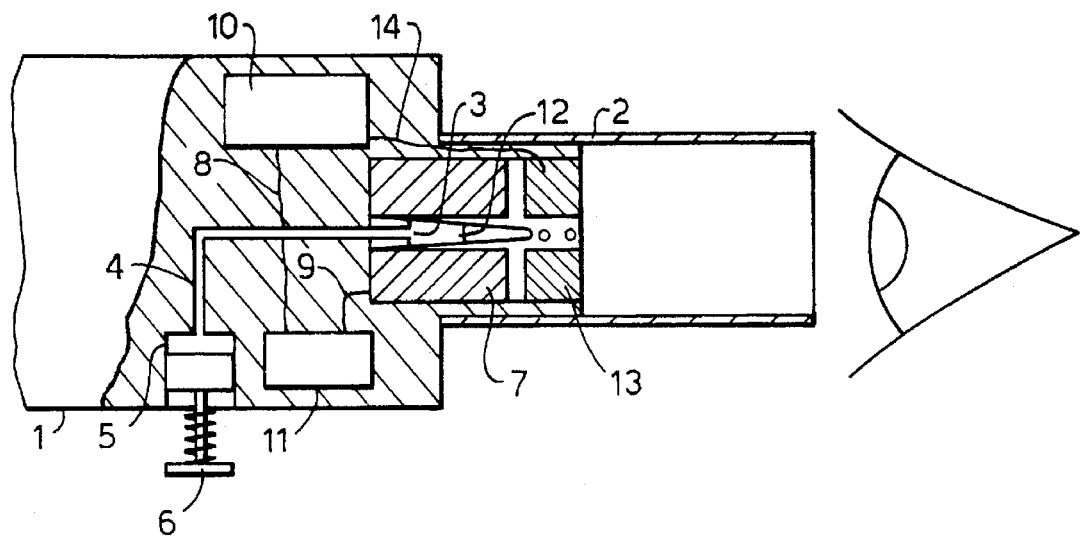

United States Patent [19]

Rowe

[11] Patent Number: 5,630,793

[45] Date of Patent: May 20, 1997

[54] AQUEOUS OPHTHALMIC SPRAYS

[75] Inventor: Raymond C. Rowe, Congleton, United Kingdom

[73] Assignee: Zeneca Limited, London, United Kingdom

[21] Appl. No.: 408,971

[22] Filed: Mar. 23, 1995

[30] Foreign Application Priority Data

Mar. 25, 1994 [GB] United Kingdom ............ 9405952

[51] Int. Cl.⁶ .................... A61N 1/30; A61M 35/00
[52] U.S. Cl. ............ 604/20; 604/289; 604/294; 604/298; 128/200.14
[58] Field of Search ................ 604/289, 290, 604/294–302

[56] References Cited

U.S. PATENT DOCUMENTS

| 4,388,343 | 6/1983 | Voss et al. |
| 4,564,016 | 1/1986 | Maurice et al. ............ 604/289 X |
| 4,952,212 | 8/1990 | Booth et al. ............ 604/294 |
| 5,053,000 | 10/1991 | Booth et al. ............ 604/294 X |
| 5,171,306 | 12/1992 | Vo ............ 604/295 |
| 5,368,582 | 11/1994 | Bertera ............ 604/295 |

FOREIGN PATENT DOCUMENTS

| 0011269 | 5/1980 | European Pat. Off. . |
| 0224352 | 6/1987 | European Pat. Off. . |
| 0389665 | 10/1990 | European Pat. Off. . |
| 0590165 | 4/1994 | European Pat. Off. . |
| 1271341 | 9/1960 | France . |
| 8500761 | 2/1985 | WIPO . |

OTHER PUBLICATIONS

M. Döring, "Flüssigkeiten mikrofein dosieren", F&M Feinwerktechnik & Messtechnik, Nov., 1991, pp. 459–463.
Choi et al, "Generation of controllable monodispersed sprays using impulse jet and charging techniques", Review of Scientific Instruments, Jun. 1990, pp. 1689–1693.
"Non–Impact Printing", pp.310,321.
"Further Applications of Charged Drops" pp. 163–171.
"Miscellaneous Applications", pp. 204–207.

*Primary Examiner*—Sam Rimell
*Assistant Examiner*—Robert V. Racunas
*Attorney, Agent, or Firm*—Cushman Darby & Cushman Intellectual Property Group of Pillsbury Madison & Sutro, LLP

[57] ABSTRACT

A method of administering to the eye a liquid ophthalmic formulation, comprising an ophthalmologically acceptable liquid and optionally containing an ophthalmologically-active substance, characterized in that the formulation has a viscosity in the range $10^{-3}$ to 1.0 Pa.s and a resistivity lower than $10^4$ ohm.cm, and that a jet of the formulation is ejected towards the eye, from a spray nozzle situated adjacent to a piezoelectric or electromagnetic transducer, to form a stream of uniformly-sized, equally spaced, uncharged droplets, the stream of uncharged droplets is subsequently directed past a charging electrode to induce an electric charge on each droplet in the stream, and the charged droplets discharge their electric charge by earthing on contact with the eye; and spraying apparatus suitable for use in that method.

12 Claims, 1 Drawing Sheet

AQUEOUS OPHTHALMIC SPRAYS

This invention relates to a method of spraying aqueous solutions or suspensions to the eye, and apparatus suitable for the delivery of such sprays.

BACKGROUND OF THE INVENTION

A conventional method of ocular administration of aqueous solutions or suspensions comprises the use of eye drops. This is generally known to have low patient acceptability, especially in the young, and it is necessary, for administration, to incline the recipient's head towards a horizontal position. The administration of a large drop of liquid to the eye initiates a blink reflex, which can result in a substantial wastage of the applied liquid or suspension by drainage either through the tear ducts or onto the skin surface. Indeed, it has been reported that if a 30–50 µl drop is applied to the eye, the actual volume that remains at the target is only 5–7 µl. Therefore, in addition to the low patient acceptability, there is a 4-to 10-fold wastage. This leads to inefficiency in the use of expensive ingredients and, in addition, the administrator has little control, and is uncertain, over the amount of liquid which actually reaches the target. This is particularly important if the liquid is a solution or suspension of an ophthalmologically-active therapeutic substance.

Another conventional method of ocular administration of an ophthalmologically-active therapeutic substance comprises the use of an ointment. This similarly has been found to have low patient acceptability and, in this method also, a substantial wastage of active ingredient can result.

These problems in the efficient administration of therapeutically active substances to the eye are largely overcome in European Patent No. 0 224 352B by generating a spray of electrically charged droplets of a liquid formulation comprising an ophthalmologically-active substance and an ophthalmologically-acceptable diluent, for subsequent administration to the eye. The formulation has a viscosity in the range $10^{-3}$ to 1.0 Pa.s at 25° C., and a resistivity in the range $10^4$ to $10^{12}$ ohm.cm at 25° C. The formulation is applied to a spray nozzle wherein a sufficiently large electrical potential relative to earth is applied to the formulation from a high voltage generator, that sufficient electrical gradient is produced at the nozzle to atomize the formulation as a spray of electrically charged droplets.

Although such a method allows the delivery to the eye of an optimum small volume of a formulation of a therapeutic substance, without requiring the recipient's head to be inclined towards the horizontal, it does, however, still have some drawbacks. Solutions or suspensions containing more than about 50% of water, that is, of lower resistivity than $10^4$ ohm.cm, cannot be sprayed, and high voltages of 15 kV or higher are used. Further, an electrode needs to be in contact with the formulation, to achieve the correct voltage for atomization, and this could cause cross-contamination problems for pharmaceutical formulations. A further disadvantage is that a formulation containing substantial amounts of non-aqueous solvents, which is to be dispensed by this method, is likely to be hypertonic, which although acceptable for very low volume applications can result in a stinging sensation if larger volumes are administered to the eye.

SUMMARY OF THE INVENTION

The present invention provides accurate dispensing of a low volume of a solution or suspension to the eye without the above-mentioned drawbacks. In particular the present invention allows the dispensing of isotonic solutions, which avoids stinging sensations, it allows the use of suspensions as well as solutions, and it offers manufacturing and environmental advantages by the reduced use of non-aqueous solvents. This is achieved by a process which involves the production of a colinear stream of uniformly-sized, equally spaced droplets of a liquid formulation, using either piezoelectric or electromagnetic transducers to cause uniform break-up of a jet of the formulation emitted from a nozzle. The droplets so produced are initially not electrically charged, and charging is accomplished subsequently by passing the stream of droplets through a cylindrical charging electrode longitudinally positioned so that induced electric charges are trapped on the droplets as they pass through the cylindrical electrode.

As indicated above, conventional methods for ocular administration lead to wastage of ingredient, for example by drainage through the naso-lachrymal duct into the throat, and subsequent ingestion into the gastro-intestinal tract, whence it can be absorbed systemically and exert undesired side-effects. For example, it is well documented in the literature that β-adrenoceptor antagonists administered as eye-drops can exert a significant cardiovascular effect as a result of such ingestion into the gastro-intestinal tract.

The present invention enables accurate targetting of a fine spray of electrically charged droplets of a liquid formulation to dose just the required amount of an ophthalmologically active substance, thereby substantially eliminating unwanted side-effects.

Thus, according to the invention, there is provided a method of administering to the eye a liquid ophthalmic formulation, comprising an ophthalmologically acceptable liquid and optionally containing an ophthalmologically-active substance, characterized in that the formulation has a viscosity in the range $10^{-3}$ to 1.0 Pa.s and a resistivity lower than $10^4$ ohm.cm, and that a jet of the formulation is ejected towards the eye, from a spray nozzle situated adjacent to a piezoelectric or electromagnetic transducer, to form a stream of uniformly-sized, equally spaced, uncharged droplets, the stream of uncharged droplets is subsequently directed past a charging electrode to induce an electric charge on each droplet in the stream, and the charged droplets discharge their electric charge by earthing on contact with the eye.

The method may be carried out in a unit dose mode, by charging the nozzle with a unit dose from an external source each time it is used, or in multi-dose mode, in which case a reservoir of the formulation supplies a unit dose to the spray nozzle each time the method is carried out.

The liquid ophthalmic formulation may be a hygiene product, for example an eyewash or artificial tears for the treatment of dry eye, or a moistening or lubricating product for contact lens users, in the form of a conventional, predominantly aqueous and essentially isotonic liquid preparation, or it may be a product containing an ophthalmologically-active substance.

The ophthalmologically active substances encompassed by this invention are any compounds having a pharmacological effect on and/or in the eye. Typical of such compounds are chemotherapeutic agents, compounds to aid ocular examination, and compounds to aid surgery, for example:

(a) anti-inflammatory agents, such as prednisolone and other corticosteroids;

(b) antimicrobial drugs, such as antibiotics, antiseptics, antivirals, fungicides and sulphonamides, for example chloramphenicol, sulphacetamide, gentamycin, nystatin, acyclovir and idoxuridine;

(c) autonomic drugs, such as β-adrenoceptor antagonists, cycloplegics, miotics, mydriatics and vasoconstrictors, for example timolol, atenolol, pilocarpine, atropine, tropicamide, hyoscine, ephedrine, phenylephrine, carbachol, guanethidine and adrenaline;

(d) local anaesthetics, such as lignocaine or oxybuprocaine;

(e) diagnostics, such as fluorescein;

(f) drugs to assist healing of corneal abrasions, such as urogastrone and epidermal growth factor (EGF);

of which (c) is a particularly important group.

Suitably, the ophthalmologically active substance is present in the formulation in a concentration range of from about 0.1% to about 20%, and preferably from about 5% to about 10%, but the required concentration depends, naturally, upon the potency of the particular active substance being used.

A resistivity lower than $10^4$ ohm.cm for the liquid ophthalmic formulation is achieved by making it predominantly aqueous, although a small proportion of non-aqueous liquids, up to about 20%, may also be incorporated. Suitable such non-aqueous liquids are, for example, glycerol, propylene glycol, polyethylene glycol of average molecular weight up to about 600, and dimethyl isosorbide.

The viscosity of the formulation may be adjusted to within the required range by the addition of viscolysers, for example hydroxyethylcellulose, hydroxypropylcellulose, carboxymethylcellutose, hydroxypropylmethylcellulose, methylcellulose, polyvinyl alcohol, polyethylene glycol, dextran or polyvinylpyrrolidone.

The tonicity of the formulation may be adjusted into the range tolerated by the eye, for example tonicity equivalent to 0.2–1.4% w/v sodium chloride, by the addition of a tonicity modifier. A preferred range of tonicity is equivalent to from 0.6–1.0% w/v sodium chloride, and especially preferred are solutions having a tonicity as close as possible to 0.9% w/v sodium chloride. A suitable tonicity modifier is, for example, sodium chloride itself. The addition of sodium chloride as a tonicity modifier also has the effect of lowering the resistivity of the formulation.

The formulation may also contain a preservative, for example benzalkonium chloride, chlorhexidine acetate, phenylmercuric acetate, phenylmercuric nitrate, thiomersal, chlorbutol, benzyl alcohol or p-hydroxybenzoates.

The formulation may also contain a pH buffer salt, to maintain the pH of the formulation at an optimum to minimize chemical degradation, to increase comfort for the user, and to enhance therapeutic effect. Suitable such buffer salts are, for example, borate buffer (boric acid/borax), phosphate buffer (sodium hydrogen phosphate/sodium phosphate) and citrate buffer (citric acid/sodium citrate).

Several drugs used in ophthalmic formulations oxidize on exposure to air, with loss of potency, and the formulation may therefore advantageously contain an antioxidant, for example sodium metabisulfite for acid formulations, or sodium sulfite for alkaline formulations.

A chelating agent, for example disodium edetate, may also be included, to remove traces of heavy metals, where the presence of such impurities catalyses the breakdown of the drug. Disodium edetate also has the effect of enhancing the activity of certain preservatives, and the concentration of benzalkonium chloride, for example, may be reduced when disodium edetate is also present in the formulation.

According to a further feature of the invention there is provided an apparatus for carrying out the method described above. The invention thus provides spraying apparatus for dispensing a liquid formulation to the eye, as described above, which comprises:

(i) at least one spray nozzle having an outlet of sufficiently small cross section to be capable of retaining an appropriate amount of a liquid formulation, by surface tension;

(ii) means to supply an appropriate measured volume of a liquid formulation to the spray nozzle;

(iii) means to eject a measured volume of liquid formulation from the spray nozzle as a jet;

(iv) means for exciting the jet of liquid formulation emitted from the spray nozzle to form a stream of droplets of liquid formulation;

(v) a charging electrode spaced co-axially in front of the spray nozzle, and so spaced that the stream of droplets, immediately they are formed, are within the charging field of the electrode; and (vi) means for applying a voltage to the electrode.

In one embodiment of this invention, the means to supply an appropriate measured volume of a liquid formulation is provided by a metered valve or syringe-pump of the type used for multi-dose administration of insulin, to control the passage of the liquid formulation from a reservoir in the apparatus, to the spray nozzle. Alternatively, accurately measured low volumes can be supplied to the apparatus by placing the spray nozzle in the liquid formulation and drawing in the required volume by pipette action, for example by using a piston in a syringe.

In a preferred aspect of this invention, we have found that the best spraying results are achieved using a modification of the previous apparatus, in which the spray nozzle is demountable from the apparatus. In use the required volume of formulation is placed in the demounted spray nozzle, which is then located on the spraying apparatus in any convenient manner, such as by screwing or by friction-fit on an appropriate receiving member. In this way, the low volume of formulation is measured in any convenient manner prior to use.

Piston action can also be used as the means to eject a measured volume of liquid formulation from the spray nozzle as a jet.

The means for exciting the jet of liquid formulation emitted from the spray nozzle to form a stream of droplets of liquid formulation may, for example, a piezoelectric or an electromagnetic transducer. For optimum droplet generation, the jet of liquid formulation needs to be perturbed at a wavelength equal to 9.016 times the radius of the spray nozzle, so that, for example, for a nozzle of approximately 100 μm diameter, frequencies of 1–200 kHz, preferably 50–150 kHz, are required.

The charging electrode which is spaced co-axially in front of the spray nozzle conveniently takes the form of a cylinder or annulus, co-axial with the spray nozzle, charged to a suitable positive or negative potential, but it may also be in the form of separate elements of any suitable form, located around the axis of the nozzle, and with a space between, through which the stream of droplets can be directed in order to acquire an electrical charge. As indicated above, for efficient use of the formulation, that is, so that all of the active ingredient reaches the treatment site, it is necessary that each droplet in the stream becomes electrically charged as soon as it is formed from the jet, so the charging electrode must be located in front of the nozzle so that immediately a droplet is formed, it is within the charging field of the charging electrode.

The resistivity of the liquid formulation must be chosen to be low enough to ensure that the droplets become fully charged within the duration of the charging electrode pulse, which will typically be 2–4 μs. It can be shown mathematically that, for a given geometry, the charge on the droplets is determined solely by the voltage applied to the charging electrode. For droplets of approximately 100 μm diameter, charging voltages in the range of about 0.1 to about 1000 V are suitable, modulated at the same frequency as the drop generation rate, that is, the transducer frequency, or some sub-harmonic of it. Resistivities for the liquid formulation of less than $10^4$ ohm.cm, and preferably in the range of $10^2$ to $10^3$ ohm.cm, are required in order for the droplets to become fully charged.

Generally, in the apparatus of this invention, at least the spray nozzle is suitable to be hand-held when in use, and comprises one or two spray nozzles, depending upon whether it is desired to treat eyes separately or concurrently. Conveniently, the voltage required to charge the charging electrode is provided by a battery powered voltage generator, housed in hand-held apparatus. In another embodiment, the voltage can be generated in a remote pack, and supplied by an electrical connection to a hand-held spraying apparatus. In another embodiment, the reservoir supplying the formulation to the spray nozzle may be remote from the hand-held spray nozzle, and connected thereto by appropriate flexible tubing. In another embodiment, both the voltage generator and the reservoir may be remote from the hand-held spray nozzle.

BRIEF DESCRIPTION OF THE DRAWINGS

A particular embodiment will now be described, by way of example only, with reference to FIG. 1, which is a schematic view illustrating the principal components of one form of the apparatus.

FIG. 2 illustrate mydriatic response measurements.

DETAILED DESCRIPTION OF THE PREFERRED EMBODIMENTS

Referring to FIG. 1, there is a body member 1 of a suitable size to be hand-held. On one wall of the body member 1 there is mounted a guide 2 in the form of a short tube, the diameter of which approximates to the size of the eye to be treated. In the portion of the wall of the body member 1 which lies within the guide tube 2 there is positioned centrally the outlet 3 of a narrow bore tube 4 which at its other end broadens to provide a wider bore section 5, positioned in a side wall of the body member 1, and in which a spring-loaded piston 6 can operate. Located in the wall of the body member 1, and disposed around the outlet 3 of the narrow bore tube 4 in an annular manner is a piezoelectric or electromagnetic transducer 7, which is powered through electrical connections 8 and 9 from a voltage generator 10 via a frequency control unit 11, both of which are housed within the body member 1. A demountable nozzle 12 is provided which is capable of being detached from the apparatus in order to be charged with the formulation to be administered, and then re-attached securely within the central orifice of the transducer, by a tight push fit, to cooperate with the outlet 3 of the narrow bore tube 4. Within the guide tube 2, adjacent to the transducer 7 and separated therefrom by a small distance, is an annular or cylindrical charging electrode 13, located co-axially with the transducer 7, and electrically insulated from the other parts of the apparatus. The charging electrode 13 is charged to suitable positive or negative potential through an electrical connection 14 from the voltage generator 10, and its pulse frequency is controlled through the frequency control unit 11.

In use, the demountable nozzle 12 is filled with the appropriate volume of the formulation to be administered, the apparatus is held in the hand, and the guide tube is positioned directed towards the eye to be treated, and a short distance therefrom. The voltage generator 10 is switched on, to activate the transducer 7 and the charging electrode 13. The piston 6 is then depressed against its spring, to create sufficient pressure within the narrow bore tube 4 to expel the liquid formulation from the nozzle 12, through the central orifice of the transducer 7, whereby the jet of liquid formulation is broken up to produce a colinear stream of uniformly sized, equally spaced, uncharged droplets. The stream of droplets then passes through the bore of the annular charging electrode 13, where each droplet acquires an electric charge. The frequency control unit 11 is pre-adjusted to ensure that the voltage on the charge electrode is varied at the same frequency as, or a greater frequency than, that at which the droplets are produced, so that each droplet is individually electrically charged. The charged droplets then continue towards the eye to be treated, where they discharge their electric charge at the first earthed surface they encounter, namely the tissue of the eyeball, to give the eyeball an even coating of the formulation, without sensation.

The invention will now be illustrated, but not limited, by the following Example:

EXAMPLE 1

Ephedrine hydrochloride (0.25 mg) was formulated as a 5% solution in physiological saline, radiolabelled with approximately 0.8 Gbq of $^{99m}$Tc-DTPA complex. This formulation was sprayed, from apparatus essentially as hereinbefore described in this specification, onto one eye of each of 6 New Zealand white rabbits, according to the following procedure:

The test animals were acclimatised to the experimental conditions, by exposure to constant light intensity and minimal distractions, for 20 minutes. They were then placed in restraining boxes which were positioned approximately 30–40 cm in front of a camera (Pentax ME Super 35 mm camera fitted with an SMC Pentax 50 mm lens and 2× converter) set up on a tripod. A scale of known magnitude was placed next to, and in the same plane as, the pupil, prior to photographs being taken.

The animals were allowed to settle, and photographs were taken at f12 and 1/15 second, using ISO400 film (Kodak Gold 400). Photographs were taken 5 minutes prior to dosing of the ephedrine formulation, in order to allow determination of baseline (control) pupil diameters. The ephedrine formulation (5 μl) was then administered to the eye as a pulse of charged droplets generated from the apparatus of the invention described above, and photographs taken at intervals over the next 3 hours.

Pupil diameters were determined from the developed colour prints (approximately 15×10 cm) using an electronic micrometer (Digimatic Caliper, Mitutoyo Corp., Japan). Absolute pupil diameters were established by comparing the pupil diameter with the known scale on the photographs. From these measurements, the maximum response ratio was determined from the relationship:

$$RR_{max}=(\text{pupil diameter at time } t)-(\text{average pupil diameter at time } t_0)\ (\text{average pupil diameter at time } t_0)$$

The following results were obtained:

| | RRmax | | | | | | | |
|---|---|---|---|---|---|---|---|---|
| | Animal No. | | | | | | | |
| Time (min) | 1 | 2 | 3 | 4 | 5 | 6 | Mean | SD* |
| 0 | 0.00 | 0.00 | 0.00 | 0.00 | −0.04 | 0.00 | −0.01 | 0.01 |
| 18 | 0.09 | 0.03 | 0.11 | 0.40 | 0.17 | 0.11 | 0.15 | 0.13 |
| 38 | 0.24 | −0.15 | 0.15 | 0.48 | 0.13 | 0.11 | 0.16 | 0.20 |
| 59 | 0.35 | 0.29 | 0.09 | 0.52 | 0.15 | 0.15 | 0.25 | 0.16 |
| 80 | 0.14 | −0.05 | 0.03 | 0.18 | −0.16 | 0.10 | 0.04 | 0.13 |
| 102 | 0.11 | −0.07 | 0.01 | 0.15 | 0.02 | 0.02 | 0.04 | 0.08 |
| 120 | 0.13 | −0.06 | 0.13 | 0.01 | 0.05 | −0.03 | 0.04 | 0.08 |
| 140 | 0.11 | −0.11 | 0.02 | 0.25 | −0.02 | — | 0.05 | 0.13 |
| 160 | 0.10 | −0.12 | 0.11 | 0.15 | −0.14 | −0.08 | 0.00 | 0.13 |
| 180 | 0.04 | −0.14 | −0.02 | 0.26 | −0.11 | −0.12 | −0.02 | 0.14 |

*= standard deviation.

Figure 2:
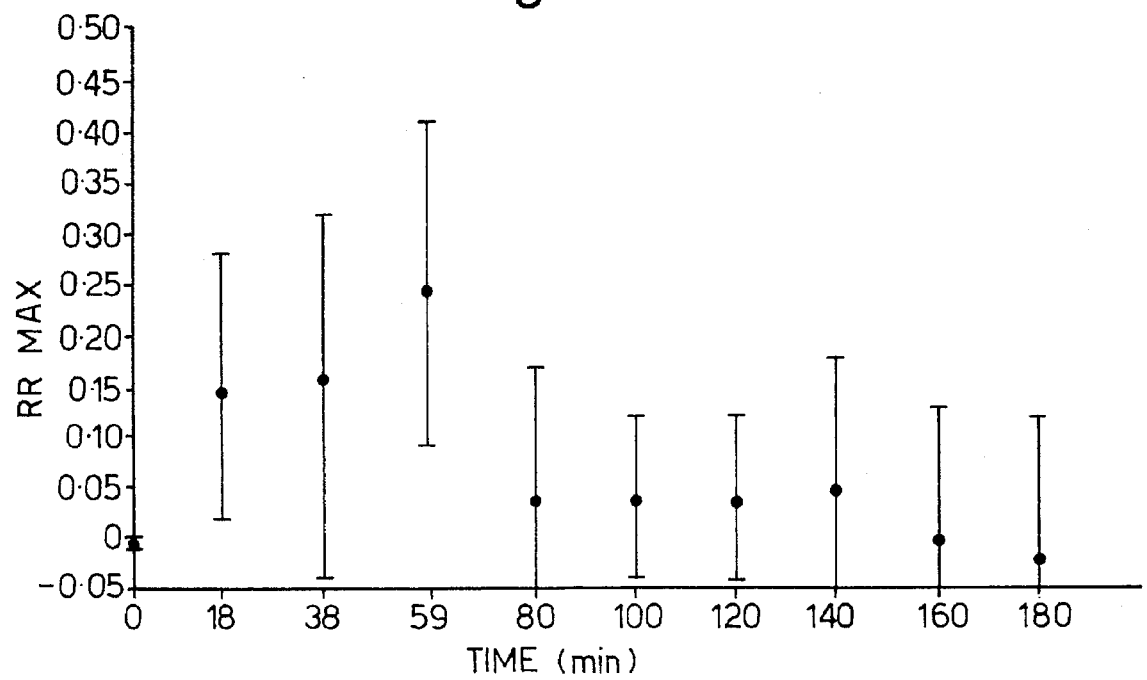

These results are presented graphically in FIG. 2, and show a marked mydriatic response in the measurements taken at 18, 38 and 59 minutes in all animals, and a continuing effect up to 80 minutes in some animals, after the administration of only 5 μl of the ephedrine formulation by the method of this invention, which is a much lower volume than that normally required with conventional modes of application.

I claim:

1. A method for administering a liquid ophthalmic formulation to the surface of the eye, said method comprising the steps of:

providing a spray nozzle having a liquid outlet in proximity to but spaced from said surface, said nozzle being situated adjacent to a piezoelectric or electromagnetic transducer;

providing to said nozzle said liquid ophthalmic formulation comprising an ophthalmologically-acceptable liquid having a viscosity in the range $10^{-3}$ to 1.0 Pa.s and a resistivity lower than $10^4$ ohm.cm;

ejecting a jet of said formulation from said spray nozzle towards said surface, forming a stream of uniformly-sized, equally spaced, uncharged droplets by means of said transducer; and causing said droplets, upon formation, to pass through the charging field of a charging electrode, thereby inducing an electric charge on each droplet before contacting said surface; whereby the charged droplets discharge their electric charge by earthing on contact with the surface of said eye.

2. A method as claimed in claim 1 wherein the liquid ophthalmic formulation is a hygiene product.

3. A method as claimed in claim 1 wherein the liquid ophthalmic formulation is a product containing an ophthalmologically-active substance.

4. A method as claimed in claim 3 wherein the ophthalmologically-active substance is selected from anti-inflammatory agents, antimicrobial drugs, autonomic drugs, local anaesthetics, diagnostics and drugs to assist the healing of corneal abrasions.

5. Apparatus for treating an eye by administering a measured volume of a liquid ophthalmic formulation to the surface of said eye, comprising:

at least one spray nozzle having a liquid outlet having an interior cross section adapted to retain therein a measured volume of a liquid formulation by surface tension;

means to supply said measured volume of liquid formulation to said spray nozzle;

means to eject said measured volume of liquid formulation from said spray nozzle outlet as a jet;

a piezoelectric or electromagnetic transducer adapted to excite said jet of liquid formulation to form a stream of droplets of said liquid formulation;

a charging electrode spaced co-axially in front of said spray nozzle outlet and adapted so that said droplets, upon formation, are charged by said electrode; and means to apply a voltage to said electrode; said apparatus being adapted, when said nozzle outlet is in a spaced relationship with said surface, to direct said droplets toward said surface, and to permit said charged droplets to discharge their electric charge by earthing on contact with the surface of said eye.

6. Apparatus as claimed in claim 5 wherein the measured volume of the formulation is supplied to the nozzle by a metered valve or syringe pump.

7. Apparatus as claimed in claim 5 wherein the measured volume of the formulation is supplied by drawing into the nozzle the required amount from an external source by pipette action.

8. Apparatus as claimed in claim 5 where the measured volume of the formulation is contained in a demountable spray nozzle which is locatable on an appropriate receiving member in the apparatus.

9. Apparatus as claimed in claim 5 wherein the piezoelectric or electromagnetic transducer is adapted to excite the liquid jet formulation at a frequency of 1–200 kHz.

10. Apparatus as claimed in claim 5 wherein the charging electrode is in the form of a cylinder or annulus charged to a voltage of between 0.1 and 1000 v.

11. Apparatus as claimed in claim 5 wherein at least the spray nozzle is suitable to be hand-held when in use.

12. Apparatus for treating an eye by administering a measured volume of a liquid ophthalmic formulation to the surface of said eye, said apparatus comprising:

a body member, of a suitable size to be hand-held in use, having a tubular guide with one end thereof mounted on a first exterior wall of said body member, the other end of said guide being open and having a diameter approximating to the size of the eye surface to be treated;

a narrow bore tube positioned in said body member and having an outlet end extending through said exterior wall substantially coaxial with and in open communication with said guide, said tube having an inlet end in open communication with a wider bore tubular section having a spring-loaded piston, located in and operable from a second exterior wall of said body member;

an annular piezoelectric or electromagnetic transducer attached to said body member, and having a central orifice, coaxial with and in open communication with the outlet end of said tube and with said guide;

a nozzle detachably attached to said body member within the central orifice of said transducer, coaxial with and in communication with said tube outlet, said nozzle being adapted to be detached from said body member in order to be charged with the formulation to be administered and then re-attached thereto;

a voltage generator adapted to power said transducer through electrical connections via a frequency control unit, said generator and control unit being positioned within said body member; and an annular charging electrode located within the tubular guide, having a central opening coaxial with the central orifice of said transducer, said electrode being in a spaced relationship with said transducer and electrically insulated said body member, tubular nozzle, transducer and nozzle, and said electrode being adapted to receive a positive or negative electrical charge from said voltage generator with said charge having a pulse frequency controlled through said frequency control unit.

* * * * *